United States Patent [19]

Burdick

[11] Patent Number: 4,498,590
[45] Date of Patent: Feb. 12, 1985

[54] PACKAGING FOR HEALTH CARE PRODUCTS

[76] Inventor: Laura M. Burdick, 330 4th Ave. #B, Venice, Calif. 90291

[21] Appl. No.: 478,755

[22] Filed: Mar. 25, 1983

[51] Int. Cl.³ .................. A45C 11/00; B65D 85/00
[52] U.S. Cl. .................................. 206/581; 229/52 B
[58] Field of Search .................. 206/570, 581, 370; 217/18; 190/48; 229/52 B, 52 BC

[56] References Cited

U.S. PATENT DOCUMENTS 1,206,276 11/1916 Wablach ............................ 190/48
2,090,882 8/1937 Zimmerman .................. 229/52 BC
3,258,017 6/1966 Albert .............................. 206/581
3,613,871 10/1971 Evans ................................ 217/18

FOREIGN PATENT DOCUMENTS 200739 11/1958 Austria ............................. 206/370

Primary Examiner—William T. Dixson, Jr.
Attorney, Agent, or Firm—Romney Golant Martin & Ashen

[57] ABSTRACT

An improved packaging for health care products such as self-administrable health tests which are designed to be used separate and apart from the outer package, including a lower base compartment for holding the products, and an upper auxiliary compartment formed by two side panels and two end panels which are manually movable between a closed position with the panels in upwardly convergent disposition to an open position with the panels in non-convergent position to allow manual and visual access to the products. An inner package insert is preferably included to separately hold the products in easy identifiable locations before and after use.

15 Claims, 8 Drawing Figures

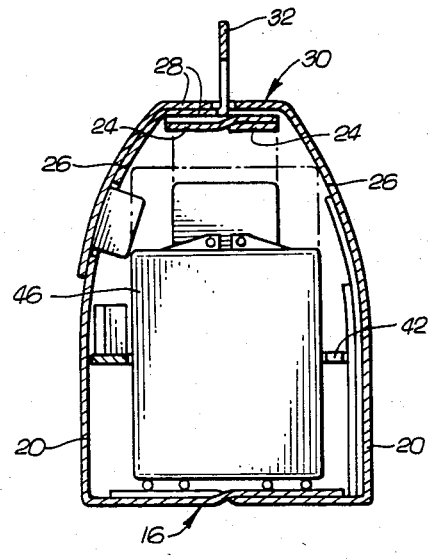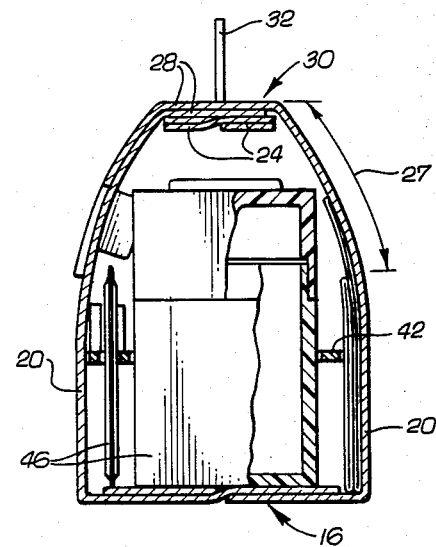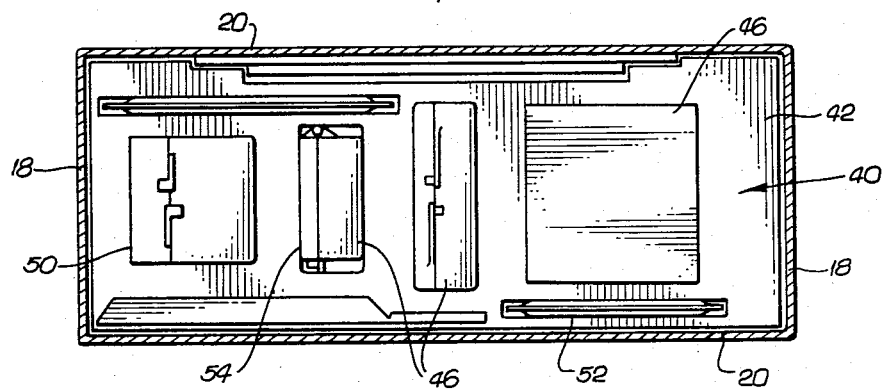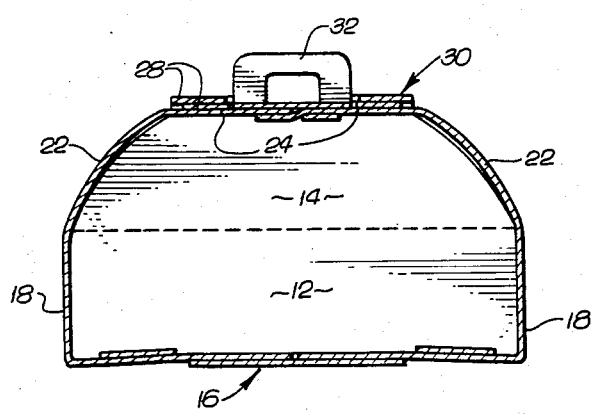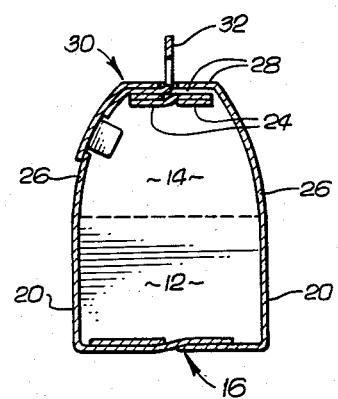

PACKAGING FOR HEALTH CARE PRODUCTS

This invention relates generally to packaging for health care products, and more specifically to reusable packaging for a plurality of health care items which can be separately and/or collectively removed when the package is in an open position, and which are securely held and stored when the package is in a closed position.

Generally speaking, most health care products such as first aid kits and adhesive bandages are packaged in conventional boxes which must be sifted through in order to find the particular item desired, and which do not hold the items separately and securely in fixed positions when the package is tipped and/or otherwise jostled around between use or during shipping and storage.

As more and more health care products are being marketed for use in the home by consumers, it becomes increasingly important to safely and securely package such items in order to avoid the disadvantages of conventional boxes, containers and packaging. Also, safe and accurate use is very important, and conventional types of containers do not allow easy visual and manual access to the package contents for removal of certain items before use as well as for repackaging of the re-usable items for future use.

Therefore, it is a principal object of this invention to provide improved packaging which will restrain and secure various health care products of diverse sizes and shapes during shipping and storage while at the same time expose such products to visual identification and manual access to a person desiring to use certain one of said products, usually after the products have been removed from the packaging, and then allowing easy return of the reusable items to the package after use.

In the Drawing:

FIG. 4 is a sectional view of the outer package member taken along the line 4—4 in FIG. 3 showing a top plan view of typical health care products in receptacles located in the inner package insert;

FIG. 5 is a cross-sectional view of the outer package member and inner package insert taken along the line 5—5 in FIG. 3 showing a partially cut-away view of a typical health care product positioned in the inner package insert;

FIG. 6 is a cross-sectional view of the outer package member and inner package insert taken along the line 6—6 in FIG. 3;

FIG. 7 is a longitudinal sectional view of an empty outer package member; and

FIG. 8 is a cross sectional view of an empty outer package member.

Figure 1:
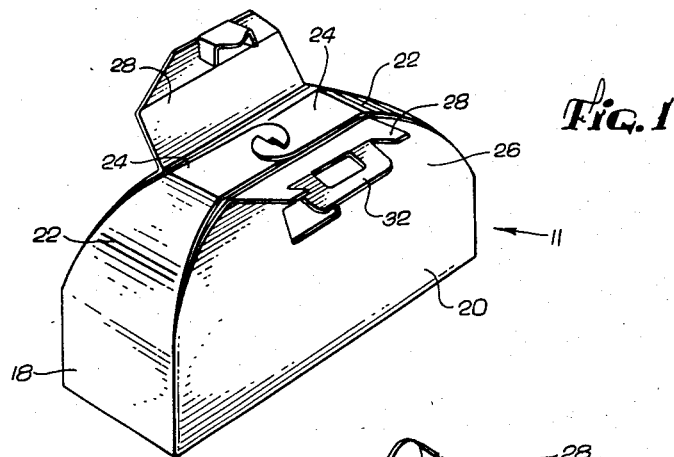
FIG. 1 is a perspective view of a presently preferred embodiment of the invention showing an outer package member in partially closed position.

Referring to the illustrated embodiment shown in the drawing, an outer package member 11 is provided which incorporates various folding and attachment techniques which are well known in the trade, and therefore the details of such techniques will not be discussed in detail. What is believed to be important is the overall shape of the package itself as well as the relative sizes and shapes of the component portions which by manual manipulation allow the package to be converted between an enclosed or closed position on the one hand for shipping and storage to an accessible or open position on the other for inspection, identification, removal and replacement of certain ones of the health care items located in the packaging.

The outer package 11 incorporates a base or foot compartment 12 and communicating therewith an auxiliary or head compartment 14. The foot compartment 12 is in the form of a rectangular box which remains in substantially the same shape and configuration in both the open and closed positions, and is defined by a floor 16, end walls 18 and side walls 20 which are of greater length than the end walls when measured in the horizontal direction.

The head portion 14 is formed by extensions of the lower walls 18, 20. These include end panels 22 having an upward linear dimension 23 terminating at a junction line with end flaps 24 which can be joined together to form a lid 30 as shown in FIG. 1. The head portion 14 is also formed by extensions which are side panels 26 having an upward linear dimension 27 terminating at a junction with side flaps 28 which can be joined together to also form the lid 30 and which include a projection which in the closed position constitutes a handle 32 (see FIG. 7).

Figure 2:
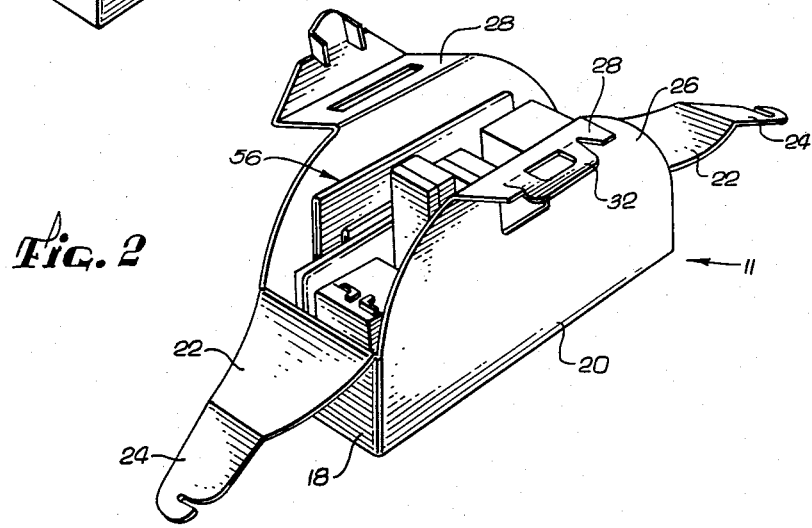
FIG. 2 is the same view as FIG. 1 with the outer package member in open position revealing a group of typical health care products therein.
Figure 3:
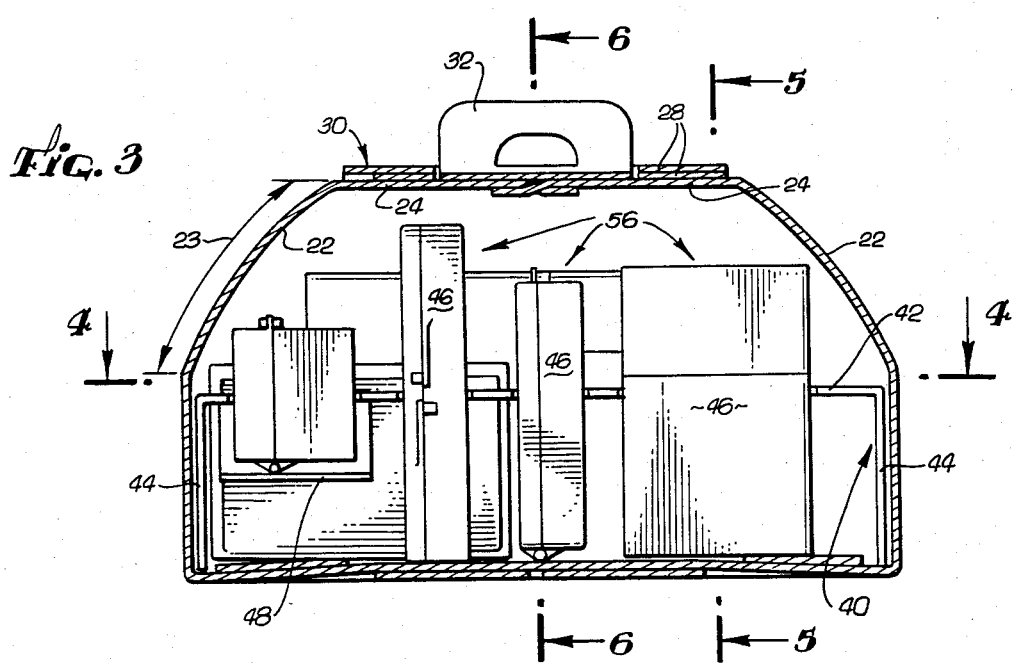
FIG. 3 is a longitudinal sectional view of the outer package member in closed position showing a side view of a plurality of typical health care products in receptacles located in an inner package insert.

It will be appreciated from the drawing, as best shown in FIG. 2, that by making the outer package in the proportions of the invention, with the upward linear dimension 23 greater than the upward linear dimension 27, the end panels have a greater angle of convergence in the closed position than do the side panels. Moreover, by making the lateral dimension of the end panels relatively narrow, the end panels are easily bent into a non-convergent position when the package is in the open position to allow easy visual and manual access both from the top as well as laterally into the auxiliary compartment.

Accordingly, the outer package constitutes an important component of the invention which by itself constitutes an improved structure for enclosing health care products in a base compartment which communicates upwardly with an auxiliary compartment having varied vertical heights to provide restrained movement for the variously sized product items projecting from the base compartment up into the auxiliary compartment. Morever, by disengaging the flaps, the end panels are easily movable in opposite directions to open up the top and sides of the upper compartment for virtually complete accessibility, and the side panels flex back to their normally upright position to further expand such accessibility.

In the exemplary embodiment, and in order to more fully take advantage of the improved aforesaid features of the outer packaging, the invention provides inner packaging inserts such as 40 which typically may include a horizontal panel 42 and support legs 44 for resting on the floor 16 of the outer package member. While the invention is applicable to various types of inserts, the presently preferred bype especially useful for self administrable health tests includes variously shaped receptacles 46 for holding the product items. The inside dimension of the outer package 11 is correlated with the outer dimension of the various health care items 56 so that upward movement of the items is restrained by the outer package before the items become dislodged from their respective receptacles in the packaging positioner or insert 40. Thus, by providing a truncated receptacle such as 48, even smaller items will be restrained from excessive movement by one of the uper boundary panels enclosing the upper chamber. Alternatively, cut-outs can be made to form receptacles near the end as shown at 50 or near the side as shown at 52 for shorter items or more centrally located as at 54 for the taller items. Thus, in addition to the upper restraint provided by the lid 30, the inwardly tapered panels 22,26 also provide such restraint when the package is in the closed position.

In the preferred form, the inner packaging positioner 40 is located completely within the base compartment so that the only things projecting into the upper compartment are the health care items themselves, thus facilitating the easy identification by label, color coding, or otherwise the particular item of items which are necessary to be removed from the packaging. After use, the unused or reusable items are easily returned to their proper location for secure and safe storage after the package has been returned to its closed position.

Although an exemplary embodiment of the invention has been disclosed for illustrating purposes, it will be understood that various changes, modifications, and substitutions may be incoporated in such embodiment without departing from the invention as defined by the claims hereinafter.

I claim as my invention:

1. Improved packaging for a plurality of health care products which are designed to be removed from such packaging before being put to their intended use, including:

an outer container member having lower wall means for defining a foot portion and having upper wall means for defining a head portion, and which is manually convertible between an open position where said lower wall means remains intact while said upper wall means are partially displaced outwardly to allow easy removability of the health care products and a closed position to securely store the health care products when not in use;

an inner positioning member located in said foot portion, and having separator means for separately positioning each item of the health care products in said foot portion in a substantially upright position extending above said foot portion into said head portion to facilitate visual inspection of and manual access to each item of the health care products when said outer container member is in said open position; and said upper wall means includes a pair of opposing side panels which constitute an upward extension of said lower wall means and which remain upstanding when said outer container is in the open position, and opposing end panel means movable from being non-convergent when said outer container member is in said open position to being upwardly convergent to be removably attachable together by flap means for forming a lid above said head portion when said outer container is in said closed position, with said opposing end means having a width less than the width of said opposing side panels, and with both opposing side panels and said opposing end means for enclosing said head portion when said outer container member is in said closed position and for limiting the upward movement of the health care products relative to said inner position member to prevent each item of the health care products from becoming accidentally dislodged from its storage position in said inner positioning member.

2. The packaging of claim 1 wherein said end panels have a greater upward linear dimension than said side panels.

3. The packaging of claim 1 wherein said end panels have a greater angle of convergence than said side panels when said outer container member is in said closed position.

4. The packaging of claim 1 wherein said end panels are bendable away from each other to be relatively divergent when said outer container member is in said open position.

5. The packaging of claim 1 wherein said flap means includes a handle projecting upwardly from said lid.

6. The packaging of claim 1 wherein said inner positioning member includes a horizontal insert panel removably disposed in said foot portion of said outer container member and having support legs for holding said insert panel a predetermined distance above the bottom of said foot portion.

7. The packaging of claim 6 wherein said insert panel includes centrally located receptacles for receiving relatively tall items of the health care products.

8. The packaging of claim 6 wherein said insert panel includes peripherally located receptacles for receiving relatively short items of the health care products.

9. The packaging of claim 6 wherein said insert panel includes truncated receptacles for receiving extremely short items of the health care products.

10. Improved packaging for health care products including:

rectangular box means for defining a base storage compartment for holding the health care products, said box means including a floor having a side dimension substantially greater than its end dimension, a pair of upstanding side walls, and a pair of upstanding end walls, with said rectangular box means remaining intact and unchanged when the packaging is in either a closed position for storage of the health care products or an open position for access to and use of the health care products;

side panel means constituting an upward extension of said side walls, said side panel means remaining substantially upright both when the packaging is in the open position and in the closed position; and end panel means constituting an upward extension of said end walls, and combining together with said side panel means for forming an auxiliary compartment above and communicating with said base storage compartment, with said end panel means being manually bendable along its junction with said adjoining upstanding wall and movable between the closed position for enclosing the health care products within said storage and auxiliary compartments and the open position for allowing manual and visual access into said auxiliary compartment.

11. The improved packaging of claim 10 including at least one end panel member movable away from the adjacent side panel means to a non-upright position for allowing lateral access to the auxiliary compartment when said end panel means is in said open position, while leaving said rectangular box means intact with its side walls and end walls still upstanding.

12. The improved packaging of claim 10 wherein said end panel means includes two opposing end panels which are upwardly convergent when said end panel means is in said closed position.

13. The improved packaging of claim 12 wherein said end panels are non-convergent when said end panel means are in said open position.

14. The improved packaging of claim 10 wherein said side panel means includes two opposing side panels which are upwardly convergent when said end panel means is in said closed position.

15. The improved packaging of claim 10 further including positioner means located within said rectangular box means for holding and positioning the health care products to be inside of said base storage compartment and said auxiliary compartment.

* * * * *